United States Patent
Cafferata

(10) Patent No.: US 6,689,121 B1
(45) Date of Patent: Feb. 10, 2004

(54) SYSTEMS AND METHODS FOR TREATING ISCHEMIA

(75) Inventor: Robert L. Cafferata, Belmont, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/159,834

(22) Filed: Sep. 24, 1998

(51) Int. Cl.⁷ .............................. A61F 2/02; A61K 9/22
(52) U.S. Cl. .................................... 604/891.1; 424/423
(58) Field of Search ................. 424/426, 423, 424/424; 604/892.1, 890.1, 891.1

(56) References Cited

U.S. PATENT DOCUMENTS

| | | |
|---|---|---|
| 3,680,544 A | 8/1972 | Shinnick et al. |
| 3,991,750 A | 11/1976 | Vickery |
| 3,995,617 A | 12/1976 | Watkins et al. |
| 4,307,722 A | 12/1981 | Evans et al. |
| 4,451,253 A | 5/1984 | Harman |
| 4,461,280 A | 7/1984 | Baumgartner |
| 4,503,569 A | 3/1985 | Dotter |
| 4,546,499 A | 10/1985 | Possis |
| 4,562,597 A | 1/1986 | Possis et al. |
| 4,580,568 A | 4/1986 | Gianturco |
| 4,582,181 A | 4/1986 | Samson |
| 4,641,653 A | 2/1987 | Rockey |
| 4,649,922 A | 3/1987 | Wiktor |
| 4,655,771 A | 4/1987 | Wallsten |
| 4,658,817 A | 4/1987 | Hardy et al. |
| 4,665,918 A | 5/1987 | Garza et al. |
| 4,681,110 A | 7/1987 | Wiktor et al. |
| 4,700,692 A | 10/1987 | Baumgartner |
| 4,718,425 A | 1/1988 | Tamaka et al. |
| 4,733,665 A | 3/1988 | Palmaz |
| 4,768,507 A | 9/1988 | Fischell et al. |
| 4,774,949 A | 10/1988 | Fogarty |
| 4,785,815 A | 11/1988 | Cohen |
| 4,791,939 A | 12/1988 | Maillard |
| 4,813,925 A | 3/1989 | Anderson, Jr. et al. |
| 4,852,580 A | 8/1989 | Wood |
| 4,861,330 A | 8/1989 | Voss |
| 4,889,137 A | 12/1989 | Kolobow |
| 4,894,057 A | 1/1990 | Howes |
| 4,917,666 A | 4/1990 | Solar et al. |
| 4,920,980 A | 5/1990 | Jackowski |
| 4,950,227 A | 8/1990 | Savin et al. |
| 4,995,857 A | 2/1991 | Arnold |
| 4,997,431 A | 3/1991 | Isner et al. |
| 5,040,543 A | 8/1991 | Badera et al. |
| 5,042,486 A | 8/1991 | Pfeiler et al. |

(List continued on next page.)

FOREIGN PATENT DOCUMENTS

| | | |
|---|---|---|
| DE | 19703482 A1 | 1/1997 |
| DE | 296 19 029 u1 | 4/1997 |
| EP | 0 132 387 | 1/1985 |
| EP | 0 363 661 | 4/1990 |
| EP | 0 490 459 A1 | 6/1992 |

(List continued on next page.)

OTHER PUBLICATIONS

Abstracts from the 70th Scientific Sessions, Orange County Convention Center, Orlando, Florida, Nov. 9–12, 1997: Supplement to Circulation, Vo. 96: No. 8, Oct. 21, 1997.

Neil B. Ingels, et al., *Measurement of Midwall Myocardial Dynamics in Intact Man by Radiography Of Surgically Implanted Markers*, Circulation, vol. 52, pp. 859–867 (Nov. 1975).

Wilensky, et al., "Methods and Devices for Local Drug Delivery in Coronary and Peripheral Arteries", Trend Cardiovasc Med, vol. 3, No. 5, 1993, pp. 163–170.

(List continued on next page.)

*Primary Examiner*—Weilun Lo

(57) ABSTRACT

A system and method for implanting pellets into myocardial tissue for treatment of coronary artery restenosis, ischemic heart disease, or cardiac conduction of disturbances. The mechanism of delivery can be transcatheter via chambers of the heart, endoscopic pericardial approach via minimally invasive transthoracic access, or intraoperative pericardial approach during open-chest surgery. Noncardiac tissues can also be treated.

15 Claims, 4 Drawing Sheets

U.S. PATENT DOCUMENTS

| | | |
|---|---|---|
| 5,047,028 A | 9/1991 | Gian |
| 5,049,138 A | 9/1991 | Chevalier et al. |
| 5,056,517 A | 10/1991 | Fenici |
| 5,087,243 A | 2/1992 | Avitall |
| 5,098,374 A | 3/1992 | Othel-Jacobsen et al. |
| 5,114,414 A | 5/1992 | Buchbinder |
| 5,158,548 A | 10/1992 | Lau et al. |
| 5,167,614 A | 12/1992 | Tessman et al. |
| 5,172,699 A | 12/1992 | Svenson |
| 5,176,626 A | 1/1993 | Soehendra |
| 5,180,366 A | 1/1993 | Woods |
| 5,190,058 A | 3/1993 | Jones et al. |
| 5,256,146 A | 10/1993 | Ensminger et al. |
| 5,266,073 A | 11/1993 | Wall |
| 5,269,326 A | 12/1993 | Verrier |
| 5,287,861 A | 2/1994 | Wilk |
| 5,290,295 A | 3/1994 | Querals et al. |
| 5,312,456 A | 5/1994 | Reed et al. |
| 5,324,325 A | 6/1994 | Moaddeb |
| 5,328,470 A | 7/1994 | Nabel et al. |
| 5,372,600 A | 12/1994 | Beyar et al. |
| 5,380,316 A | 1/1995 | Alta et al. |
| 5,386,828 A | 2/1995 | Owens et al. |
| 5,389,096 A | 2/1995 | Alta et al. |
| 5,391,199 A | 2/1995 | Ben-Haim |
| 5,405,376 A | 4/1995 | Mulier et al. |
| 5,409,004 A | 4/1995 | Sloan |
| 5,409,019 A | 4/1995 | Wilk |
| 5,423,885 A | 6/1995 | Williams |
| 5,425,757 A | 6/1995 | Tiefenbrun et al. |
| 5,429,144 A | 7/1995 | Wilk |
| 5,441,516 A | 8/1995 | Wang et al. |
| 5,452,733 A | 9/1995 | Sterman |
| 5,453,090 A | 9/1995 | Martinez et al. |
| 5,458,615 A | 10/1995 | Klemm |
| 5,464,404 A | 11/1995 | Abela et al. |
| 5,464,650 A | 11/1995 | Berg et al. |
| 5,466,242 A | 11/1995 | Mori |
| 5,476,505 A | 12/1995 | Limon |
| 5,480,422 A | 1/1996 | Ben-Halm |
| 5,487,739 A | 1/1996 | Aebischer et al. |
| 5,501,664 A | 3/1996 | Kaldany |
| 5,514,176 A | 5/1996 | Bosley, Jr. et al. |
| 5,551,427 A | 9/1996 | Altman |
| 5,551,954 A | 9/1996 | Buscemi et al. |
| 5,558,091 A | 9/1996 | Acker et al. |
| 5,562,613 A | 10/1996 | Kaldany |
| 5,562,619 A | 10/1996 | Mirarchi et al. |
| 5,562,922 A | 10/1996 | Lambert |
| 5,569,272 A | 10/1996 | Reed |
| 5,571,168 A | 11/1996 | Toro |
| 5,593,412 A | 1/1997 | Martinez et al. |
| 5,593,434 A | 1/1997 | Williams |
| 5,602,301 A | 2/1997 | Field |
| 5,614,206 A | 3/1997 | Randolph et al. |
| 5,629,008 A * | 5/1997 | Lee .................. 424/426 |
| 5,643,308 A | 7/1997 | Markman |
| 5,653,756 A | 8/1997 | Clarke et al. |
| 5,655,548 A | 8/1997 | Nelson |
| 5,656,029 A | 8/1997 | Imran et al. |
| 5,662,124 A | 9/1997 | Wilk |
| 5,666,970 A | 9/1997 | Smith |
| 5,676,850 A | 10/1997 | Reed et al. |
| 5,980,548 A | 10/1997 | Evans |
| 5,682,906 A | 11/1997 | Sterman et al. |
| 5,690,643 A | 11/1997 | Wijay |
| 5,735,897 A | 4/1998 | Buirge |
| 5,741,330 A | 4/1998 | Brauker et al. |
| 5,744,515 A | 4/1998 | Clapper |
| 5,755,682 A | 5/1998 | Knudson et al. |
| 5,756,127 A | 5/1998 | Grisoni et al. |
| 5,769,843 A | 6/1998 | Abela et al. |
| 5,782,823 A | 7/1998 | Mueller |
| 5,785,702 A | 7/1998 | Murphy et al. |
| 5,792,453 A | 8/1998 | Hammond et al. |
| 5,797,870 A | 8/1998 | March et al. |
| 5,807,384 A | 9/1998 | Mueller |
| 5,810,836 A | 9/1998 | Hussein |
| 5,817,101 A | 10/1998 | Fiedler |
| 5,824,049 A | 10/1998 | Ragheb et al. |
| 5,824,071 A | 10/1998 | Nelson et al. |
| 5,830,502 A | 11/1998 | Dong et al. |
| 5,833,608 A | 11/1998 | Acker |
| 5,840,059 A | 11/1998 | March et al. |
| 5,861,032 A | 1/1999 | Subramaniam |
| 5,879,383 A | 3/1999 | Bruchman et al. |
| 5,899,915 A | 5/1999 | Saadat |
| 5,971,993 A | 10/1999 | Hussein et al. |
| 6,045,565 A | 4/2000 | Ellis et al. |
| 6,197,324 B1 * | 3/2001 | Crittenden |
| 6,251,418 B1 * | 6/2001 | Ahern et al. |
| 6,263,880 B1 | 7/2001 | Parker et al. |

FOREIGN PATENT DOCUMENTS

| | | |
|---|---|---|
| EP | 0 515 867 A2 | 12/1992 |
| EP | 0 714 640 A1 | 6/1996 |
| EP | 0 717 969 A2 | 6/1996 |
| EP | 0 732 089 A2 | 9/1996 |
| EP | 0 207 438 | 1/1997 |
| EP | 0 812 574 A2 | 12/1997 |
| EP | 0 830 873 A2 | 3/1998 |
| EP | 0 853 921 A2 | 7/1998 |
| EP | 0 953 320 A2 | 11/1999 |
| FR | 2725 615 | 10/1994 |
| FR | 1.278.969 | 1/2001 |
| RU | 2026640 C1 | 1/1995 |
| RU | 2063179 C1 | 7/1996 |
| WO | WO 89/01798 | 3/1989 |
| WO | WO 90/06723 | 6/1990 |
| WO | WO 91/15254 | 10/1991 |
| WO | WO 94/05265 | 3/1994 |
| WO | WO 94/27612 | 12/1994 |
| WO | WO 95/33511 | 12/1995 |
| WO | WO 96/20698 | 7/1996 |
| WO | WO 96/39830 | 12/1996 |
| WO | WO 96/40368 | 12/1996 |
| WO | WO 97/16169 | 5/1997 |
| WO | WO 97/42910 | 7/1997 |
| WO | WO 97/32551 | 9/1997 |
| WO | WO 97/38730 | 10/1997 |
| WO | WO 97/44071 | 11/1997 |
| WO | WO 97/45105 | 12/1997 |
| WO | WO 97/47253 | 12/1997 |
| WO | WO 98/05307 | 2/1998 |
| WO | WO 98/08456 | 3/1998 |
| WO | WO 98/16644 | 4/1998 |
| WO | WO 98/23228 | 6/1998 |
| WO | WO 98/25533 | 6/1998 |
| WO | WO 98/29148 | 7/1998 |
| WO | WO 98/32859 | 7/1998 |
| WO | WO 98/46115 | 10/1998 |
| WO | WO 99/21510 | 5/1999 |
| WO | WO 99/38459 | 8/1999 |
| WO | WO 99/53863 | 10/1999 |
| WO | WO 99/55252 | 11/1999 |

OTHER PUBLICATIONS

Ranade, "Drug Delivery Systems: 3A. Role of Polymers in Drug Delivery", J Clin Pharmacol, 1990; 31:10–23.

Folkman, et al., "Blood Vessel Formation: What Is Its Molecular Basis?" Cell, vol. 87, 1153–1155, Dec. 27, 1996.

Knighton, et al., "Wound Healing Angiogenesis: Indirect Stimulation by basic Fibroblast Growth Factor", The Journal of Trauma, vol. 30, 1990, pp. S134–144.

Gibbons, et al., "Molecular Therapies for Vascular Diseases", Science, vol. 272, May 3, 1996, pp. 689–693.

Kim, et al., "Inhibition of Vascular Endothelial Growth Factor–Induced Angiogenesis Suppresses Tumour Growth in Vivo", Nature, vol. 362, 1993, pp. 841–844.

Schumacher, et al., "Induction of Neoangiogenesis in Ischemic Myocardium by Human Growth Factors—First Clinical Results of a New Treatment of Coronary Heart Disease", Circulation, vol. 97, 1998, pp. 645–650.

Folkman, "Angiogenic Therapy of the Human Heart", Circulation, vol. 97, 1998, pp. 628–629.

Parker, et al., "Growth Factors, Proto–Oncogenes, and Plasticity of the Cardiac Phenotype", Annu. Rev. Physiol. 1991, 53:179–200.

Olwin, et al., "Art Fibroblast Growth Factors Regulators of Myogenesis In Vivo?", *Progress in Growth Factor Research*, vol. 5, 1994, pp. 145–158.

Li, et al., "Cardiomyocyte Transplantation Improves Heart Function", *Ann Thorac Surg* 1996; 62:654–661.

Aoki, et al., "Survival of Grafts of Genetically Modified Cardiac Myocytes Transfected with FITC–labeled Oligodeoxynucleotides and the—Galactosidase Gene in the Noninfarcted Area, but Not the Myocardial Infarcted Area", *Gene Therapy*, vol. 4, 1997, pp. 120–127.

Gojo, et al. "Transplantation of Genetically Marked Cardiac Muscle Cells", *J Thorac Cardiovasc Surg*, vol. 113, 1997, pp. 10–18.

Gojo, et al., "Ex Vivo Gene Transfer Into Myocardium Using Replication–Defective Retrovirus", *Cell Transportation*, vol. 5, 1996, pp. S81–S84.

Ueno, et al., "Adenovirus–Mediated Expression of the Secreted Form of Basic Fibroblast Growth Factor (FGF–2) Induces Cellular Proliferation and Angiogenesis In Vivo", *Arterioscler Thromb Vasc Biol*, vol. 17, 1997, pp. 2453–2460.

Jia, et al., "Transplanted Cardiomyocytes Survive in Scar Tissue and Improve Heart Function", *Transplantation Proceedings*, 29, 1997, 2093–2094.

Li, et al., "Natural History of Fetal Rat Cardiomyocytes Transplanted Into Adult Rat Myocardial Scar Tissue", *Circulation*, vol. 96, 1997, pp. II–179–II–187.

Ferrari, "Muscle Regeneration by Bone Marrow–Derived Myogenic Progenitors", *Science*, vol. 279, Mar. 6, 1998, pp. 1528–1530.

Penisi, "Bone Marrow Cells May provide Muscle Power", *Science*, vol. 279, Mar. 6, 1998, p. 1456.

Robinson, et al., "Arterial Delivery of Genetically Labelled Skeletal Myoblasts to the Murinew Heart: Long–Term Survival and Phenotypic Modification of Implanted Myoblasts", *Cell Transplantation*, vol. 5, No. 1, 1996, pp. 77–91.

Arras, et al., "The Delivery of Angiogenic Factors to the Heart by Microsphere Therapy", *Nature Biotechnology*, vol. 16, Feb. 1998, pp. 159–162.

Waller, "Anatomy, Histology, and Pathology of the Major Epicardial Coronary Arteries Relevant to Echocardiographic Imaging Techniques", *J Am Soc Echo* 1989; 2:232–52.

Smith, "Adult Rat Cardiomyocyte Proliferation Assay", *In Vitro Cell Dev Biol*, vol. 33, Jun. 1997, pp. 428–431.

"Time Release Pellets for Biomedical Research" 2000 Catalog, Innovative Research of America, 2 N. Tamiami Trail, Ste 404, Sarasota, Florida 34236.

A. Sachinopoulou et al., *Invited Review Transmyocardial Revascularization*, Lasers in Medical Science 1995, vol. 10, pp. 83–91, Sep. 1995.

B. Schumacher et al., *Induction of Neoangiogenesis in Ischemic Myocardium by Human Growth Factors, First Clinical Results of a New Treatment of Coronary Heart Disease*, Clinical Investigation and Reports, pp. 645–650, Dec. 1997.

Garrett Lee et al., *Feasibility of Intravascular Laser Irradiation for In Vivo Visualization and Therapy of Cardiocirculatory Diseases*, American Heart Journal, vol. 103, No. 6, pp. 1076–1077.

Garrett Lee et al., *Laser–Dissolution of Coronary Atherosclerotic Obstruction*, American Heart Journal, vol. 102, No. 6, part 1, pp. 1074–1075, Dec. 1981.

George S. Abela et al., *Use of Laser Radiation to Recanalize Totally Obstructed Coronary Arteries (Abstract)*, Journal American College Cardiology 1983:1(2):691.

George S. Abela et al., *Laser Revascularization: What Are Its Prospects?*, Journal of Cardiovascular Medicine, pp. 977–984, Sep. 1983.

Isam N. Anabtawi et al., *Experimental Evaluation of Myocardial Tunnelization as a Method of Myocardial Revascularization*, Journal of Thoracic and Cardiovascular Surgery, vol. 58, No. 5, pp. 638–646, Nov. 1969.

John E. Hershey et al., *Transmyocardial Puncture Revascularization*, Geriatrics, pp. 101–108, Mar. 1969.

M. A. Martinelli, et al., *Intraluminal Ultrasound Guidance of Transverse Laser Coronary Atherectomy*, Optical Fibers in Medicine vol. 1201, pp. 68–78, (1990).

Mahmood Mirhoseini et al., *Transventricular Revascularization by Laser*, Lasers in Surgery and Medicine, vol. 2, pp.187–198, 1982.

Mahmood Mirhoseini et al., *Clinical Report: Laser Myocardial Revascularization*, Lasers in Surgery and Medicine vol. 6, pp. 459–461, 1986.

Mahmood Mirhoseini et al., *New Concepts in Revascularization of the Myocardium*, The Annals of Thoracic Surgery, vol. 45, No. 4, pp. 415–420, Apr. 1988.

Peter Whittaker, et al., *Transmural Channels Can Protect Ischemic Tissue, Assessment of Long–term Myocardial Response to Laser and Needle–Made Channels*, Circulation, vol. 93, No. 1, pp. 143–152, Jan. 1996.

P.K. Sen, et al, *Further Studies in Multiple Transmyocardial Acupuncture as a Method of Myocardial Revascularization*, Surgery, vol. 64, No. 5, pp. 861–870, Nov. 1968.

R.I. Hardy et al., *Regional Myocardial Blood Flow and Cardiac Mechanics in Dog Hearts with $CO_2$Laser–Induced Intramyocardial Revascularization*, Basic Research Cardiology, 85:179–197 (1990).

Roque Pifarre et al., *Myocardial Revascularization by Transmyocardial Acupuncture: A Physiologic Impossibility*; Journal of Thoracic and Cardiovascular Surgery; vol. 58, No. 3, pp. 424–429, Sep. 1969.

R–K Li et. al, "*Cell Trerapy to Repair Broken Hearts*" Can J. Cardiology 1998; 14(5):735–744.

Zhai Y. et. al., "*Inhibition of Angiogenesis and Breast Cancer Xenograft Tumor Growth by Vegi, A Novel Cytokine of the TNF Superfamily*", Int. J. Cancer 1999; Jul. 2;82(1):131–6.

Warejcka DJ et. al., "*A Population of Cells Isolated From Rat Heart Capable of Differentiating Into Several Mesodermal Phenotypes*", J. Surg. Res. 1996 May;62(2):233–242.

Braun T, Arnold, "*MYF–5 and MYOD Genes are Activated In Distinct Mesenchymal Stem Cells and Determine Different Skeletal Muscle Cell Lineages*", EMO J. 1996 Jan 15; 15(2):310–318.

Wakitani S. et. al., "*Myogenic Cells Derived From Rat Bone Marrow Mesenchymal Stem Cells Exposed to 5–Azacytidine*", Muscle Nerve 1995 Dec; 18(12):1417–1426.

Yamaguchi A., "*Regulation of Differentiation Pathway of Skeletal Mesenchymal Cells in Cell Lines by Transforming Growth Factor–Beta Superfamily*", Semin Cell Biol. 1995 Jun.:6(3):165–173.

Chiu RC. et. al., "*Cellular Cardiomyoplasty:Myocardial Regeneration With Satellite Cell Implantation*", Ann Thorac Surg 1995 Jul.:60(1):12–18.

Gulati AK, "*Regeneration Pattern of Cardiac and Skeletal Muscle After Transplantation Into a Skeletal Muscle Bed in Rats*", Anat Rec. 1995 Jun:242(2):188–194.

Tam SK. et. al., "*Cardiac Myocyte Terminal Differentation, Potential for Cardiac Regeneration*", Ann NY Acad. Sci. 1995 Mar 27;752:72–79.

Mima T. et. al., "*Fibroblast Growth Factor Receptor is Required for in Vivo Cardiac Myocyte Proliferation at Early Embryonic Stages of Heart Development*", Proc. Natl. Acad. Sci. USA 1995 Jan 17;92(2):467–471.

Butler R., "*Evidence for a Regenerative Capacity in Adult Mammalian Cardiac Myocytes*", Am. J. Physiol 1989 Mar;256(3 Pt. 2):R797–R800.

J. Heschler et al., "*Embryonic Stem Cells: A Model to Study Structural and Functional Properties in Cardiomyogenesis*", Cardiovascular Research 16 (1997) 149–162.

T. Maciag, "Molecular and Cellular Mechanisms of Angiogenesis".

Charles E. Murry et. al., "*Skeletal Myoblast Transplantation for Repair of Myocardial Necrosis*", The American Society for Clinical Investigation, Inc., vol. 98: No. 11: Dec.1996, 2512–2523.

Shawn W. Robinson et. al., "*Implantation of Skeletal Myoblast–Derived Cells*", Cellular Cardomyoplasty: Myocardial Repair with Cell Implantation, 1997, R.G. Landes Co., pp. 79–104.

Charles E. Murry et. al., "*Muscle Differentiation During Repair of Myocardial Necrosis in Rats Via Gene Transfer With Myod*", The American Society for Clinical Investigation, Inc., vol. 98:No. 10: Nov. 1996; pp 2209–2217.

Shinji Makino et. al., "*Establishment of a Cardiomyogenic Cell Line From Mouse Bone Marrow Stomal Cell Exposed to 5–Azacytidine*".

Joachim Burhenne, "*Less Invasive Medicine: Historical Perspectives*", Boston Scientific Online, www.bsci.com/corporate/specialreport1.html; May 20, 1999, pp. 1–8.

Charles T. Doiter, "*Transluminally–Placed Coilsping Endarterial Tube Grafts, Long–Term Patency in Canine Popliteal Artery*", Investigative Radiology, Sep.–Oct. 1969 vol. 4; pp. 329–332.

Raymond G. McKay, "*Catheter–Based Techniques of Local Drug Delivery*", The New Manual of Interventional Cardiology, 1996, pp. 645–660.

Alfred Goldman, "*Experimental Methods for Producing a Collateral Circulation to the Heart Directly From the Left Ventricle*", J. Thoracic Surg.; Mar. 1956; vol. 31. No. 3; pp. 364–374.

Vallavan Jeevanandam, "*Myocardial Revascularization by Laser–Induced Channels*", Surgical Forum, American College of Surgeons 76th Clinical Congress, pp. 225–227.

A. Hassan Khazei et al., "*Myocardial Canalization, a New Method of Myocardial Revascularization*", The Annals of Thoracic Surgery, Vo. 6, No. 2, Aug. 1968; pp. 163–171.

Ladislav Kuzela et. al. "*Experimental Evaluation of Direct Transventricular Revascularization*", Journal of Thoracic and Cardiovascular Surgery, vol. 57, No. 6, Jun. 1969.

C. Massimo et al., "*Myocardial Revascularization by a New Method of Carrying Blood Directly From the Left Ventricular Cavity Into the Coronary Circulation*", Journal Thoracic Surgery, Aug. 1957, pp. 257–264.

A. Michael Lincoff et al., "*Local Drug Delivery for the Prevention of Restenosis: Fact, Fancy and Future*", Circulation: vol. 90, No. 4: Oct. 1994.

M. Mirhoseini et al., "*Revascularization of the Heart by Laser*", Journal of Microsurgery (1981) 2:253–260.

M. Mirhoseini, "*Myocardial Revascularization by Laser: A Clinical Report*", Lasers in Surgery and Medicine (1983) 3:241–245.

Reimer Riessen et. al., "*Prospects for Site–Specific Delivery of Pharmacologic and Molecular Therapies*", JACC vol. 23, No. 5; Apr. 1994:1234–44.

P.K. Sen et. al., "*Transmyocardial Acupuncture a New Approach to Myocardial Revascularization*", Journal of Thoracic and Cardiovascular Surgery, vol. 50, No. 2, Aug. 1965.

Bruce F. Waller, "*Anatomy, Histology, and Pathology of the Major Epicardial Coronary Arteries Relevant to Echocardiographic Imaging Techniques*", Journal of the American Society of Echocardiography, vol. 2, No. 4: Jul.–Aug. 1989, pp. 232–252.

P. Walter et. al., "*Treatment of Acute Myocardial Infarction by Transmural Blood Supply From the Ventricular Cavity*", Europ. Surg. Res. 3:130–138 (1971).

Robert L. Wilensky et. al., "*Methods and Devices for Local Delivery in Coronary and Peripheral Arteries*", TCM vol. 3, No. 5 (1993) pp. 163–170.

\* cited by examiner

SYSTEMS AND METHODS FOR TREATING ISCHEMIA

FIELD OF THE INVENTION

The invention relates to the local delivery of therapeutic agents, and more particularly, to systems and methods that deliver depots of therapeutic agents into a body of tissue to allow for the treatment of a variety of conditions, including coronary conditions and cardiovascular indications.

BACKGROUND OF THE INVENTION

Disease, injury and surgery can result in localized tissue damage and morbidity. For example, the principal treatment for occlusive vascular diseases is angioplasty, a procedure in which a balloon is inserted into the vessel and then inflated to dilate the area of narrowing. During inflation, the balloon can damage the vessel wall. It appears that as a result of this damage, in 30 to 50% of cases, the initial increase in lumen dimensions is followed by a localized re-narrowing (restenosis) of the vessel over a time of three to six months. Thus, restenosis can result in the dangerous and localized renarrowing of a patient's vessel at the site of the recent angioplasty. Like many other localized diseases, restenosis is complex and at present there is no clinically effective treatment for this disease. Gibbons et al., *Molecular Therapies for Vascular Diseases*, Science vol. 272, pages 617–780 (May 1996).

Restenosis, like many other localized injuries and diseases, has responded poorly to pharmacological therapies and agents. Numerous pharmacological agents have been clinically tested, and none have demonstrated an unequivocal reduction in the incidence of restenosis. However, the failure of these pharmacological therapies may arise from the systemic intolerance of the doses required to achieve local beneficial effects or in the difficulty of providing controlled administration of proper dosages over time. Accordingly, one possible reason for the failure of these therapies is that submaximal doses of pharmacological agents are being administered to avoid the serious side-effects that might result from systemic administration of the proper dosage.

To address this problem, various researchers have proposed methods for site-specific delivery of pharmacologic and molecular therapies. These methods include the direct deposition of therapeutic agents into the arterial wall through an intravascular delivery system, systemic administration of therapeutic agents that have a specific affinity for the injured or diseased tissue, and systemic administration of inactive agents followed by local activation.

At present, systems exist that attempt to achieve localized delivery of therapeutic agents. These systems include dual balloon delivery systems that have proximal and distal balloons that are simultaneously inflated to isolate a treatment space within an arterial lumen. A catheter extends between the two balloons and includes a port that can admit within the treatment space between the balloons an aqueous medium, typically one containing a therapeutic agent. Pressure can be applied to the medium to create conditions conducive to intramural infusion. Other balloon-based localized delivery systems include porous balloon systems, hydrogel-coated balloons and porous balloons that have an interior metallic stent. Other systems include locally placed drug-loaded coated metallic stents and drug-filled polymer stents. Wilensky et al., *Methods and Devices for Local Drug Delivery in Coronary and Peripheral Arteries*, Trend Cardiovasc Med, vol. 3 (1993).

Although these systems can provide working devices for local drug delivery, the efficacy of these devices turns on, and is limited by, a number of factors including the rate of fluid flux through the vascular wall, the residence time of the deposited agent and the local conditions and vasculature of the deposition site. Essentially, the success of these systems is limited by the amount of time that a delivered drug will stay resident locally before being carried downstream by circulating blood. Further, to the extent that these systems allow the therapeutic agent to be carried away, these systems run the risk of applying a therapeutic agent to areas of the patient's vasculature where such agents may not be beneficial. Additionally, these existing systems are limited by the amount of drug that can be delivered to the diseased site. Moreover, drug filled polymer stents have structural problems that argue against their use.

Existing systems for local drug delivery, including direct deposition of therapeutic agents through an intravascular delivery system, systemic administration of therapeutic agents that have a specific affinity for the injured or diseased tissue, and systemic administration of inactive agents followed by local activation, all require a functioning vascular system for delivery of the therapeutic agent to the affected tissue. These systems, therefore, are inapplicable in conditions characterized by myocardial ischemia or infarction. When ischemic injury is of sufficient severity and duration, groups of involved cells die and myocardial infarction results. Within the ischemic area, not all cells are equally injured. As ischemia persists, there is wave-like progression of cell death or coagulation necrosis. The prospect for recovery decreases with increasing duration or severity of the ischemic insult. It is difficult to quantitate the extent to which ischemic injury will result in cell necrosis.

Reperfusion can salvage injured tissue even after some cells have become necrotic. However, following reperfusion, cells that have been already injured are particularly vulnerable to further injury. This phenomenon, termed "reperfusion injury," paradoxically results in cellular necrosis when circulation returns to a cell population that survived the initial ischemic insult. Many factors contribute to this situation. The endothelium of vessels in the reperfused region have been damaged, causing platelet adherence and leukocyte activation with inflammatory sequelae. Oxygen free radicals are released by damaged cells, causing further cell and organelle damage. The sodium-potassium pump, damaged with the initial ischemia, can lose its regulatory ability and allow free water accumulation during reperfusion, resulting in cell swelling and rupture. Unstable and leaky cell membranes can also lead to calcium accumulation within the cytoplasm with uptake of calcium into mitochondria and formation of insoluble calcium-phosphate crystals. As a consequence, there may be a population of cells killed by the initial ischemic insult, and a further population killed following reperfusion.

Both ischemia and infarction can adversely affect myocardial contractile function. The more extensive the injury, the more severe its impact on ventricular function. Following severe myocardial ischemia, there may be a reversible hypocontractile state called "hibernation," a condition of impaired contractility amenable to recovery (the so-called "stunned" myocardium, and frank myocardial infarction, characterized by cell death. Once a population of myocytes becomes necrotic, the injured tissue cannot regenerate itself; mature myocytes lack the capacity for cellular replication. The contribution these necrotic myocytes made to contractile function is, thus irreversibly lost. Restoration of functioning myocardium after frank infarction requires both a restoration of tissue perfusion and a replenishing of viable cells that can assume the contractile role of the infarcted tissues.

In view of the variety of localized cardiovascular conditions affecting human health, it would be advantageous to develop other methods of treatment for patients having localized cardiovascular conditions and in particular to develop methods of treatment that reduce adverse side effects and have heightened efficacy. It would furthermore be advantageous to permit treatment of localized cardiovascular conditions resulting from myocardial ischemia and myocardial infarction through local delivery of therapeutic agents.

SUMMARY OF THE INVENTION

It is therefore, an object of the invention to provide methods of treatment of a coronary artery or cardiac indication that provide a longer duration of drug pendency at the site of a localized disease.

It is a further object of the invention to provide systems and methods that reduce or eliminate the downstream flow of a locally delivered agent.

It is a further object of the invention to provide delivery of local therapeutic agents to areas of impaired vascularity.

It is yet a further object of the invention to allow improvement of contractile function in infarcted myocardial tissue.

Other objects of the invention will, in part, be obvious, and, in part, be shown from the following description of the systems and methods shown herein.

To these ends, the invention provides systems and methods for implanting a depot into a tissue wall to thereby deliver a therapeutic agent selected for the condition being treated. In one embodiment, the invention provides systems and methods for delivering a therapeutic agent into the myocardial tissue wall for treating various vascular conditions including restenosis, ischemic tissue, and myocardial infarction. Other applications of the systems and methods described herein include the delivery of angiogenesis compounds that can be implanted into ischemic tissue; and/or antiarrhythmic drugs that can be implanted at the sites of conduction abnormalities. A further application of the systems and methods described herein includes the delivery of cells for implantation into the myocardium, accompanied by angiogenesis compounds that will promote local circulation. Accordingly, the agent being locally delivered can depend on the application at hand, and the term agent, or therapeutic agent, as employed herein will be understood to encompass any agent capable of being locally delivered including, but not limited to, pharmaceutical compositions or formulations, viral or non-viral vectors (e.g., adenovirus vectors, retroviral vectors and the like), implantable (genetically engineered) cells, plasmid-liposome complexes or other DNA delivery complexes, oligonucleotides or any other suitable composition compatible with the subject being treated.

In one embodiment, the invention provides systems and methods for local delivery of at least two therapeutic agents, one of which promotes angiogenesis and the other of which contains cells adapted for implantation into the myocardium. The therapeutic agent that promotes angiogenesis can include any substance that induces the formation of blood vessels, including but not limited to such substances as vascular endothelial growth factor (VEGF), tumor angiogenesis factor (TAF), tumor necrosis factor (TNF), fibroblast growth factor (FGF), wound angiogenesis factor (WAF), other growth factors, and other substances including but not limited to angiogenin, fibrin, prostaglandin E and heparin.

Cells adapted for implantation into the myocardium include, but are not limited to, cardiomyocytes and their precursors, skeletal myoblast-derived cells, fibroblasts, genetically modified fibroblasts and bone marrow stromal cells and their derivatives. Cells adapted for implantation into the myocardium can be subjected to genetic manipulation prior to or subsequent to implantation.

In a further embodiment, the invention is understood as an apparatus for delivering therapeutic agents into the myocardium. These apparatus can comprise an outer mechanical element made of a biocompatible material which promotes angiogenesis locally by its contact with the myocardial tissues and further comprising an inner reservoir adapted for delivering cells adapted for implantation in the myocardial tissue. In another embodiment, the inner reservoir contains molecular ligands that possess specific affinity for the cell surface markers on circulating myocyte precursor cells, so that these cells are affixed within the reservoir and subsequently released. In a further embodiment, the biocompatible material of the apparatus comprises a drug releasing compound capable of releasing at least one therapeutic agent. In yet another embodiment, this therapeutic agent is capable of promoting angiogenesis. In a further embodiment, this apparatus is bioresorbable.

The invention can also be understood to include apparatus for delivering at least two therapeutic agents comprising a body formed of a biocompatible material containing at least one reservoir permeable to at least one therapeutic agent. The biocompatible material of the delivery system can include a drug releasing compound capable of releasing at least one therapeutic agent. Therapeutic agents released by the drug releasing compound include, but are not limited to, those capable of promoting angiogenesis. In another embodiment, at least two therapeutic agents are disposed within separate reservoirs, each reservoir permeable to the therapeutic agent within it. In a further embodiment, this apparatus is bioresorbable.

The apparatus can comprise an elongate flexible body having a proximal end and a distal end, a delivery chamber coupled to the distal end of the body and having a space for carrying the therapeutic agent, and a port for releasing the therapeutic agent therefrom. The apparatus can further include an actuator coupled to the distal delivery chamber and being capable of driving therapeutic agent through the port.

The terms proximal and distal as used herein will be understood to describe opposite ends of a device or element, and generally will be employed so that proximal is understood as "away from the heart" and distal is understood as "towards the heart" or to mean "toward the physician" and "away from the physician" respectively.

BRIEF DESCRIPTION OF THE FIGURES

The foregoing and other objects and advantages of the invention will be appreciated more fully from the following further description thereof, with reference to the accompanying drawings wherein.

DETAILED DESCRIPTION OF THE ILLUSTRATED EMBODIMENTS

To provide an overall understanding of the invention, the methods and devices illustrated herein are described with reference to the application of treating cardiac indications by implanting drug delivery pellets into myocardial tissue for the treatment of coronary artery restenosis, ischemic heart disease, cardiac conduction disturbances and other similar conditions. However, it will be understood that the systems and methods described herein are applicable to any condition that can benefit from the implanting of a depot of a therapeutic agent, and the invention is not to be limited to the applications illustrated herein. For example, the techniques herein are directly applicable for implanting therapeutic agents to stimulate angiogenesis. The techniques herein are also directly applicable to the methods for delivering therapeutic agents to infarcted myocardium where these therapeutic agents include substances for promoting angiogenesis and cells adapted for implantation in the myocardium. The techniques herein are further applicable to the manipulation of the cellular environment following ischemic injury, either to protect against reperfusion injury or to enhance recovery in the stunned myocardium.

The depot implanting systems illustrated herein include catheter systems for delivery via the chambers of the heart, endoscopic systems for pericardial approach via minimally invasive trans-thoracic access, and systems for use during intraoperative pericardial approach during open-chest surgery. In one practice, the devices deliver a plurality of pellets that surround, or partially surround, an artery being treated. This is understood to achieve the effect of implanting a drug-filled ring around the artery. The pellets remain in the myocardial tissue, and can give off drug(s) for a selected time period and then be absorbed by the body. The systems described herein can implant pellets that contain radio-opaque markers to facilitate viewing the pellets by fluoroscopy during catheter delivery.

Figure 1:
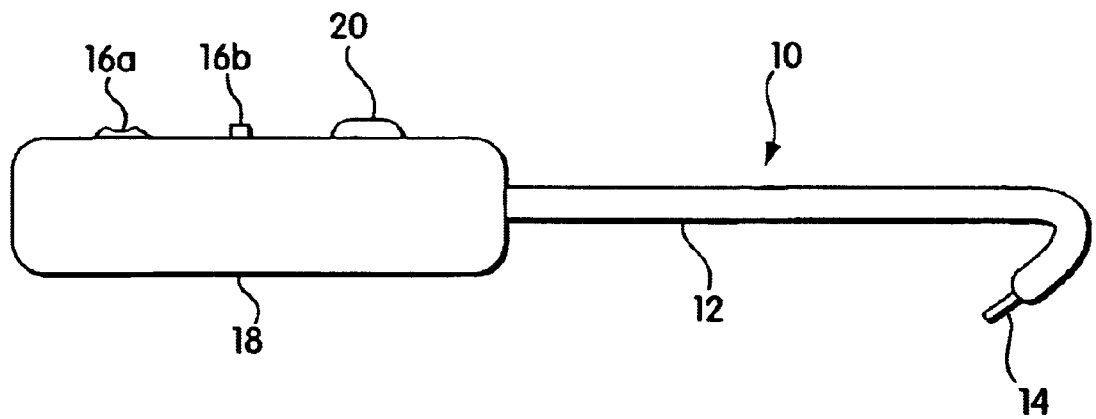
FIG. 1 depicts one embodiment of a catheter having a delivery chamber carried at the distal end.

FIG. 1 depicts one embodiment of a system for providing local delivery of a therapeutic agent. The delivery device 10 includes a catheter 12, a delivery chamber 14, steering switches 16a and 16b, a handle 18, and a delivery control switch 20.

The depicted system 10 is a catheter system that can be guided through vascular access at the femoral artery or vein of a patient until the delivery chamber 14 enters into the interior chambers of the patient's heart to implant a depot of drug within the myocardium. To that end, the catheter 12 which extends between the delivery chamber 14 and the handle 18 can be approximately 175 cm to 200 cm in length and can include an elongated rotationally rigid, longitudinally flexible body optionally made of woven polyester fibers, stainless steel wires, thermoset or thermoplastic polymers or any other material suitable for use as a catheter shaft. The catheter can have a substantially uniform diameter of approximately 0.025 to 0.100 inches (0.62 to 2.5 mm).

In the embodiment depicted in FIG. 1, the catheter 12 is a steerable catheter that allows or facilitates the guiding of the catheter through the patient's vasculature and into the chamber of the patient's heart. Further, the steerable catheter 12 allows the physician to bend the catheter once the catheter has entered into the interior of the heart, to thereby position the delivery chamber 14 adjacent the area of the endocardial wall through which the delivery chamber is to penetrate. The steering capability of the catheter 12 is illustrated by the bend located at the distal end of the catheter 12. Steering catheters suitable for use with the present invention are known in the art, and include steering catheters employed in Electrophysiology procedures. Electrophysiology catheters typically provide steering through a combination of rotation and tip bending.

One suitable steerable catheter is described in U.S. Pat. No. 5,656,029, which is incorporated herein by reference. This catheter provides an elongate flexible body that carries a bending mechanism at its distal end. The bending mechanism consists of a shape-memory element typically formed of Nitinol which is provided with a memory which makes it assume a straight condition when it is heated, such as by application of an electrical current. The shape memory element extends through the distal portion of the catheter and is adapted to remain straight along its full length in response to a current passing through the element. To control the location of the bending, an electrical bypass is slidably mounted about the bending element. The bypass element can be an elongate cylindrical sleeve formed of a conductive material and through which the bending element can extend. The bypass element can act as a short circuit that bypasses current away from the bending element. Accordingly, the bypass element prevents current from heating the bending element at the location of the bypass. Consequently, the bending element will bend at the location of the bypass. By allowing the bypass to be slid along the length of the bending element, the physician can select the location of the bypass, thereby selecting the location of bending. As the delivery chamber 14 is carried at the distal extremity of the catheter 12, this allows the physician to selectively position the delivery chamber 14 within the interior of the patient's heart.

The bending elements and bypass elements described above are carried within the catheter 12 and are not shown in FIG. 1, but however are described in detail in the above identified reference. Additionally, it is noted that although the catheter 12 has been described with reference to one type of steerable catheter it will be apparent to one of ordinary skill in the art that other suitable steering mechanisms can be employed with the present invention including steering mechanisms that include actuating poles or wires that extend longitudinally through the catheter body. Moreover, it will be further understood that although the depicted catheter 12 is optionally a steerable catheter, the devices of the invention are not to be limited to steerable devices, and will be understood to encompass conventional catheter systems as well.

Control of the depicted catheter 12 and the delivery chamber 14 is provided by the integrated hand-held control mechanism and handle 18 mounted on the proximal end of the catheter 12. The control mechanism/handle 18 can be of various types, and the depicted handle 18 is adapted for operating a steerable catheter wherein the bend of the catheter can be selectively controlled by the physician. To these ends, the hand-held contro/handle 18 is dimensionally adapted to provide the treating physician with a device that is facile to manipulate and comfortable to hold. Additionally, the hand-held mechanism/handle 18 includes a set of control switches, 16a, 16b and 20 that allow the physician to control the steering of the catheter 12 and the implanting of the depot. Switches 16a and 16b can provide steering control for the catheter 12. The switch 16a can be a slidable switch that allows the physician to control the longitudinal position of the bend within the distal tip of the catheter. The switch 16a can activate the bending mechanism to cause the catheter tip to bend as needed. The control switch 20 can activate the delivery chamber 14 to cause a pellet containing a therapeutic agent to be delivered into a tissue wall.

It will be apparent to one of ordinary skill in the art that other control mechanisms/handles can be employed with the systems of the invention without departing from the scope thereof. Specifically, other systems can include joystick controls for operating the steerable catheters and can include controls for rotating the angle at which the distal end of the catheter bends. Still other control mechanisms/handles can include pistol grips for providing manual activation of the delivery chamber 14. Other modifications and additions can be made to the control mechanism/handle without departing from the scope of the invention.

Figure 2A:
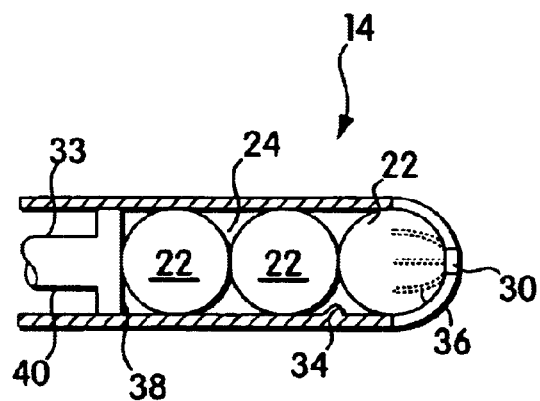
FIGS. 2A and 2B depict in more detail the delivery chamber of the catheter depicted in FIG. 1.

FIG. 2A depicts in greater detail one delivery chamber 14 which is suitable for being carried at the distal end of the catheter 12 depicted in FIG. 1. The delivery chamber 14 is sized to hold the plurality of minispheres 22, each of which contains a therapeutic agent. The minispheres 22 are carried within an interior chamber 24 which is bound at the proximal end by a plunger 33 and bound at the distal end by a wall formed of a plurality of flexible finger elements 36 that define a port 30. In the embodiment depicted in FIG. 2A, an optional detent 34 is connected to a sidewall of the chamber 24 to provide a mechanical stop that prevents the minispheres 22 from freely exiting through the port 30. Upon application of mechanical force by the plunger 33, the minispheres 22 can be pushed over the detent 34, for allowing one minisphere 22 to be ejected through port 30.

More specifically, the plunger 33 depicted in FIG. 2A includes a plate 38 and an actuating rod 40. The plate 38 is dimensioned to fill substantially the diameter of interior chamber 24 to provide thereby a surface that is adapted for forcing the minispheres 22 through the chamber 24 and out of port 30. The actuating rod 40 is connected to the plate 38 and provides a mechanical force to plate 38 to advance, or drive, the plate 38 distally into the chamber 24. In one embodiment, the actuating rod 40 extends through the catheter 12 and couples to the control mechanism/handle 18 at the proximal end of device 10. In this embodiment, the control mechanism/handle 18 includes a mechanism that drives the actuating rod 40 distally causing minispheres 22 to be delivered through port 30. Optionally, this embodiment can include a control mechanism/handle 18 that incorporates a ratchet assembly that drives the actuating rod 40 distally in discreet steps wherein a predetermined number of steps corresponds substantially to the diameter of one of the minispheres 22. For example, the depicted control switch 20 can be a rotatable switch that allows for manual actuation of a ratchet assembly contained within the control mechanism/handle 18. The ratchet assembly allows the physician to drive the plunger 33 distally into the chamber 24 thereby driving the minisphere 22 out of the port 30. In this way, the device 10 can allow for the discreet and sequential delivery of minispheres 22 from the delivery chamber 14.

In an alternative embodiment of the invention, the plunger 33 is threaded to mate with a threaded interior portion of chamber 24. Manual or motor-driven rotation of actuating rod 40 will advance or retract the plunger with a finer degree of control than that provided by strictly linear actuation. Such control over the travel distance of the plunger 33 into and out of the interior chamber 24, gives control over the number of minispheres 22 delivered through port 30.

Figure 2B:
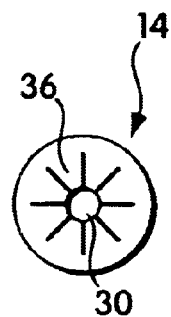

FIG. 2B provides a head-on perspective of the delivery chamber 14, showing the distal most portion of the delivery chamber 14 as viewed from a position along the longitudinal axis of the delivery chamber 14. Together, FIGS. 2A and 2B show that the distal end of the delivery chamber 14 includes a port 30 that is formed from the convergence of a plurality of flexible arched fingers 36, each of which is formed from a resilient material and each of which is biased to hold the minispheres 22 within the interior chamber 24. Upon action of the plunger 33 to move the minispheres 22 distally, the fingers 36 will yield to the axial pressure and release a minisphere 22. Additionally, in the embodiment depicted in FIG. 2A the optional detent 34 provides further resistance that prevents minispheres 22 from exiting chamber 24 through the port 30 and for providing a tactile sensation that indicates when a minisphere 22 has been released, or has become available to be released, through port 30.

The delivery chamber 14 is adapted to facilitate the implantation of a depot of drug within a tissue wall. For example the delivery chamber 14 can be sized and made of a material rigid enough to facilitate the penetration of the delivery chamber within a tissue wall. Accordingly, the depicted delivery chamber 14 can be about 0.010 to 0.050 inches in diameter, and about 0.05 to 0.075 inches in length, to have a needle-like profile that is suitable for penetrating tissue. Additionally, the depicted delivery chamber 14 can be formed of stainless steel or of plastic material that is sufficiently rigid to allow the delivery chamber 14 to pass into a tissue wall.

Figure 3A:
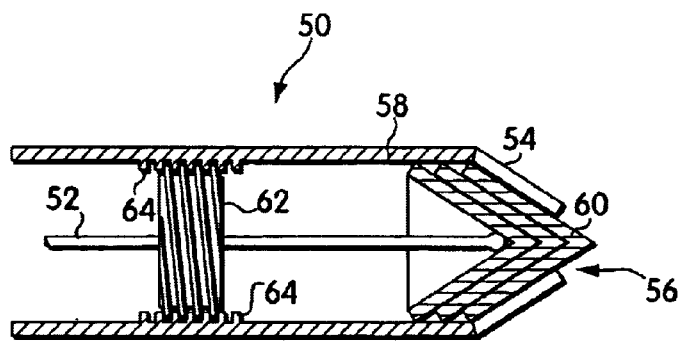
FIGS. 3A and 3B depict an alternative delivery chamber for use with the catheter of FIG. 1.
Figure 3B:
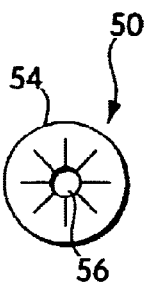

FIGS. 3A and 3B depict an alternative embodiment of a delivery chamber suitable for use with the catheter system 10 shown in FIG. 1. The depicted delivery chamber 50 includes a cylindrical sidewall 58 that defines an interior space that houses a plunger 52. The plunger 52 includes a grooved plate 62 that can be rotatably driven along the threads 64 that extend along a portion of the sidewall 58. Accordingly, in this embodiment, the plunger 52 advances into the delivery chamber 50 as the plate 62 turns across, and travels over the threads 64. The distal end of the plunger 52 butts against a stack of nested drug delivery pellets 60 and forces the pellets 60 against the elongate flexible finger elements 54 that, as shown by FIG. 3B, define the port 56.

The delivery chamber 50 implants drug pellets having a hollow, conical shape which facilitates the penetration of the implants 60 into the tissue wall. As shown, the plunger 52 can drive the pellets 60 through the port 56 and into the tissue wall. As discussed above, the flexible fingers 54 are biased to hold the pellets 60 within the chamber 50, however, the mechanical force applied by the plunger 52 will be sufficient to overcome the bias force of the fingers 54. Again as discussed above, a ratchet assembly, a rotary actuator, and/or optionally a detent, can be employed to help the physician control the number of pellets being delivered into the tissue wall. Specifically, the ratchet assembly or rotary actuator controls the distance the plunger 52 is driven into the chamber 50 and the detent provides a tactile sensation each time a pellet 60 is moved a predetermined distance.

The delivery chamber 50 provides an alternative embodiment that allows for the implantation of larger pellets of drugs where the size of the pellet may require a delivery chamber that is too large to readily penetrate through a tissue wall. Accordingly, delivery chambers can be selectively developed for the implantation systems described herein based on the applications of interest and the size of the pellet being delivered. For example, in systems that implant microspheres of drugs having diameters of about 5–15 µm, the delivery chamber can be adapted to hold the microspheres in a fluid medium and a plunger assembly, or other suitable system, can be employed to flush the microspheres from the delivery chamber and into the tissue wall. In this case, the delivery chamber can be simply a hypodermic needle, and a syringe connected to the proximal end of the system can inject the fluid medium through a lumen in the catheter 12. Other delivery chambers can be employed with the systems described herein without departing from the scope hereof.

The systems described above are capable of implanting pellets that contain a therapeutic agent. The therapeutic agent can be any compound that is biologically active and suitable for long term administration to a tissue or organ. The pellets described above can be formed as mini-spheres that are on the order of about 0.005 inches to about 0.040 inches in diameter. Particles of this size are capable of providing a therapeutically effective dose of agent and can remain where implanted, resisting fluid flux through the tissue wall.

An understanding of the technologies upon which the present invention draws is based on articles in the scientific literature, such as those cited below which are herein incorporated by reference. It is a realization of the present invention that ischemia can be treated by promoting angiogenesis in the ischemic area. It is a further realization of the present invention that the introduction of cardiomyocyte precursor cells into a damaged area of the myocardium can result in the production of functioning myocardial elements.

Molecular bases for vascular growth and remodeling have been described in the scientific literature. Folkman and D'Amore, *Blood Vessel Formation: What is its Molecular Basis?* Cell vol. 87, pages 1153–1155 (Dec. 27, 1996); Kim et al., *Inhibition of Vascular Endothelial Growth Factor-induced Angiogenesis Suppresses Tumor Growth In Vivo*, Nature vol. 362, pages 841–844 (April, 1993); Knighton et al., *Wound Healing Angiogenesis: Indirect Stimulation by Basic Fibroblast Growth Factor*, J. Trauma vol. 30, pages S134–S144 (December, 1990). These findings have been applied to the myocardium, showing that increased neovascularization can be induced by angiogenic therapy. Folkman, *Angiogenic Therapy of the Human Heart*, Circ. vol. 97, pages 628–629 (1998); Schumacher et al., *Induction of Neoangiogenesis in Ischemic Myocardium by Human Growth Factors*, Circ. vol. 97, pages 645–650 (1998). The abovementioned articles, describing the basis for applying the techniques of angiogenesis to the ischemic myocardium, are hereby incorporated by reference. In an area of the myocardium where the native circulation has been impaired, it is understood that promoting angiogenesis can lead to the ingrowth of new blood vessels and thereby can help restore the level of perfusion needed for effective tissue nutrition.

In light of the fact that mammalian cardiomyocytes are terminally differentiated early in the development of the heart, it is understood that the myocardium cannot regenerate its muscle cells after myocardial infarction. Smith and Claycomb, *Adult Rat Cardiomyocyte Proliferation Assay*, In Vitro Cell Dev. Biol. vol. 33, pages 428–431 (June, 1997); Parker and Schneider, *Growth Factors, Proto-oncogenes, and Plasticity of the Cardiac Phenotype*, Ann. Rev. Physiol. vol. 53, pages 179–200 (1991). These articles, incorporated herein by reference, describe the ways in which the functioning myocardium responds to the loss of viable cardiomyocytes following ischemic injury. Terminal differentiation, and the factors that regulate it, are described by Olwin et al, *Are Fibroblast Growth Factors Regulators of Myogenesis In Vivo?* Progress in Growth Factor Research, vol. 5, pages 145–158 (1994), incorporated herein by reference. It has been further described that transplanted myocytes can be introduced into an area of the myocardium that has been damaged by ischemia or infarction. Li et al., *Cardiomyocyte Transplantation Improves Heart Function*, Ann. Thor. Surg. vol. 62, pages 654–661 (1996). According to this article, incorporated herein by reference, cardiomyocytes are understood to survive and function when placed within an area of injured or necrotic myocardium, or within myocardial scar tissue. It has been further described that genetically modified cardiomyocytes transplanted into damaged myocardium survive in ischemic areas. Aoki et al., *Survival of Grafts of Genetically Modified Cardiac Myocytes Transfected with FITC-labeled Oligodeoxynucleotides and the Beta-Galactosidase Gene in the Noninfarcted Area but not in the Myocardial Infarcted Area*, Gene Therapy vol. 4, pages 120–127 (1997); Gojo et al., *Transplantation of Genetically Marked Cardiac Muscle Cells*, J. Thorac. Cardiovasc. Surg. vol. 113, pages 10–18 (1997); Gojo et al, *Ex Vivo Gene Transfer into Myocardium Using Replication-defective Retrovirus*, Cell Transplantation, vol. 5, pages S81–S84 (1996). These articles, incorporated herein by reference, further teach the possibility of genetic modification of cells implanted within the myocardium whereby the implanted cells would express factors that would contribute to the clinical treatment of the damaged area. Growth factors expressed by genetically modified cells are understood to produce angiogenesis in vivo. Ueno et al., *Adenovirus-Mediated Expression of the Secreted Form of Basic Fibroblast Growth Factor (FGF-2) Induces Cellular Proliferation and Angiogenesis In Vivo*, Arterioscler. Thromb. Vasc. Biol. vol. 17, pages 2453–2460 (1997).

Cardiomyocytes introduced into damaged myocardium are understood in the following articles, incorporated herein by reference, to improve cardiac function. Jia et al., *Transplanted Cardiomyocytes Survived in Scar Tissue and Improved Heart Function*, Cell Transplantation vol. 5, page 42 (1997); Li et al., *Natural History of Fetal Rat Cardiomyocytes Transplanted into Adult Rat Myocardial Scar Tissue*, Circ. vol. 96, Supp. II, pages 179–187 (1997). It is further understood, however, that other cells besides cardiomyocytes can be introduced into the damaged myocardium and will differentiate into cells that function like cardiomyocytes. Sources of cells, include the skeletal muscle satellite cells and cells from the bone marrow, are described in the following articles, incorporated herein by reference. Chiu et al., *Cellular Cardiomyoplasty: Myocardial Regeneration with Satellite Cell Implantation*, Ann. Thorac. Surg. vol. 60, pages 12–18 (1995); Ferrari et al., *Muscle Regeneration by Bone Marrow-derived Myogenic Progenitors*, Science vol. 279, pages 1528–1530 (Mar. 6, 1998); Pennisi, *Bone Marrow Cells May Provide Muscle Power*, Science vol. 279, page 1456 (Mar. 6, 1998). According to these publications, non-cardiomyocytes can be induced to differentiate into cells with structure and function analogous to cardiomyocytes, thus making a variety of cells available for transplantation into the damaged myocardium with the anticipation of functional benefit.

Methods described in the abovementioned publications for introducing cells into the myocardium have been substantially limited to direct intramural needle injections of cell suspensions under direct visualization in the operative setting. An alternative method of intra-arterial or intraventricular injection of cell suspensions into the bloodstream has been described that resulted in successful engraftation of cells within the myocardium. Robinson et al., *Arterial Delivery of Genetically Labeled Skeletal Myoblasts to the Murine Heart: Long-term Survival and Phenotypic Modification of Implanted Myoblasts*, Cell Transplantation vol. 5, pages 77–91 (1996). Microsphere technology, well-known to practitioners in the art, has been described for the delivery of angiogenic factors to the heart. Arras et al., *The Delivery of Angiogenic Factors to the Heart by Microsphere Therapy*, Nature Biotechnology vol. 16, pages 159–162 (1998). It is a realization of the present invention that the delivery of a combination of therapeutic agents, including those agents adapted for stimulating angiogenesis and those agents containing cells adapted for implantation in the myocardium, can be provided by a system of pellets that are introduced into the myocardium. The teachings of the abovementioned articles are incorporated herein by reference.

The pellets described above can be adapted for delivery of a combination of therapeutic agents, including those agents capable of stimulating angiogenesis and those agents containing cells adapted for implantation in the myocardium. In one embodiment, the pellet can be formed of a biocompatible material with a plurality of surfaces contacting the tissues of the myocardium and thereby promoting localized angiogenesis. A biocompatible material as described herein is one that does not incite systemic toxic reactions. In this embodiment, the pellet contains an inner reservoir that delivers into the myocardium cells adapted for implantation. In yet another embodiment, the pellet can be formed to contain at least one inner reservoir which contains at least one therapeutic agent. In this embodiment, the reservoir is permeable to at least one of the therapeutic agents it contains. For example, cells adapted for implantation in the myocardium can be contained in this reservoir, to be delivered into the surrounding tissues by permeating the reservoir wall. Alternatively, the pellet or the reservoir within it may be made of a bioresorbable material, holding the cells inside until it has undergone some degree of resorption. The reservoir can contain molecular ligands that have affinity for surface markers of circulating myocyte precursor cells, so these cells become enclosed within the reservoir until their release.

In another embodiment, the delivery system includes a pellet made of a biocompatible material that contains at least one reservoir permeable to at least one of the therapeutic agents it contains. Within this pellet are at least two therapeutic agents, one agent capable of promoting angiogenesis and another agent containing cells adapted for implantation in the myocardium. In one embodiment, the pellet contains at least two reservoirs, with one therapeutic agent disposed in each. These reservoirs can have different permeability characteristics, so there is differential release of the two agents. In one embodiment, the pellet includes a drug releasing compound capable of releasing at least one therapeutic agent, while the other agent is retained within a reservoir contained within the pellet. The pellet or any reservoir within it can be made of a bioresorbable material. The reservoir can contain molecular ligands that have affinity for surface markers of circulating myocyte precursor cells, so these cells become enclosed within the reservoir until their release.

Figure 4A:
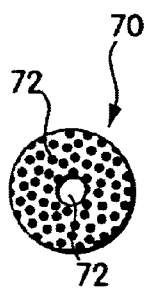
FIGS. 4A and 4B depict two embodiments of pellets suitable for implantation by the catheter of FIG. 1.

Techniques and materials for forming pellets capable of acting as drug delivery implants are well known in the art. In one practice, a solid pellet is formed from a biodegradable polymer that has been doped or "seeded" with the desired therapeutic agent. Typically, the polymer is a synthetic polymer, such as poly(lactic acid) or polyorthoesters, and is formed by solvent evaporation, spray drying, or phase separation. Such a pellet 70 is depicted in FIG. 4A. The polymer is capable of breaking down over time, allowing the drug to be released into the adjacent tissue. To aid in visualizing the implant by fluoroscopy or x-ray, a sphere of a precious metal, such as gold or platinum, can be covered with the drug-filled polymer 72 in a thickness that provides the desired volume, dosage and/or time release profile. Other acceptable drug delivery implants include the "container" implant which is filled with a liquid drug. A wall of the container is at least partially made of a biodegradable polymer that permits passage of drug molecules at a certain rate. This design is common for injectable microspheres. One advantage is that it can work for drugs that are not amenable to doping in polymers because of heat processes or other incompatibilities. A radio-opaque metal core could be incorporated into this "container" type pellet to facilitate viewing.

Additionally, pellets delivered into or against the tissue wall can be coated with or include adhesive materials that adhere to tissue. Further, coatings can be provided that facilitate the absorption of the pellet into the tissue wall. Such coatings can include fumaric acid, sebacic acid and other similar materials.

Figure 4B:
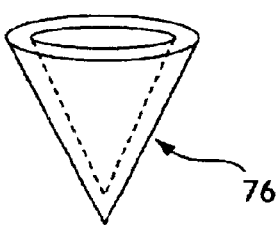

FIG. 4B depicts in more detail a pellet 76 suitable for delivery by the delivery chamber 50 depicted in FIGS. 3A and 3B. The pellet 76 is a hollow conical body that provides a pointed end that facilitates delivery of the pellet 76 into a tissue wall. Optionally, the pellet 76 can carry a radio opaque marker (not shown) and, in one embodiment, the radio opaque marker comprises grains of a noble metal which are incorporated into the material of which the pellet 76 is formed.

It will be apparent to one of ordinary skill in the art that other drug delivery implants can be employed with the systems described herein, including disc shaped pills or cylindrical implants that incorporate a solid, drug-filled polymer core with the container-type biodegradable polymer wall. One such implant is described in U.S. Pat. No. 5,629,008, which is incorporated herein in its entirety by reference.

Figure 5:
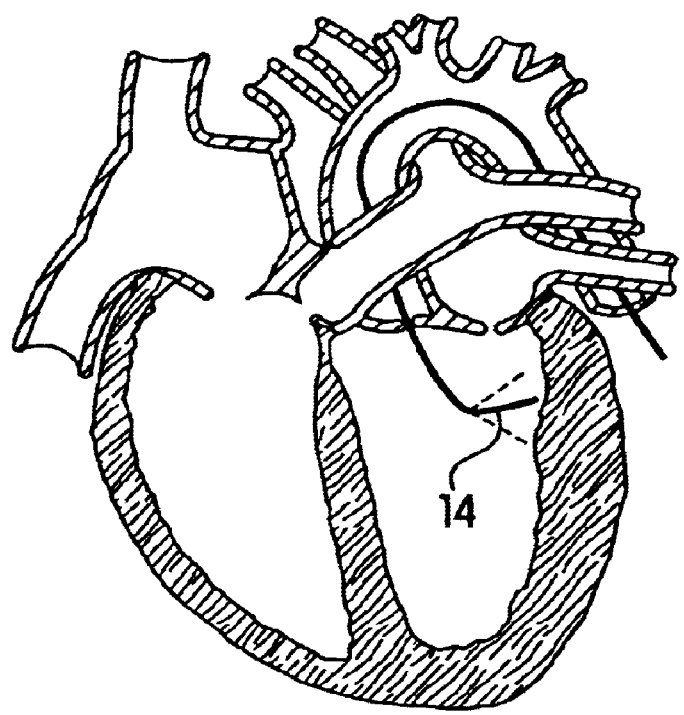
FIG. 5 depicts one method for delivering a therapeutic agent to the myocardium.
Figure 6:
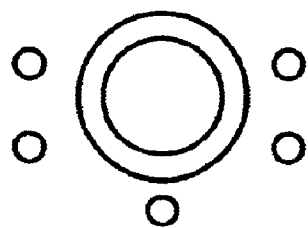
FIG. 6 provides a cross-cut perspective of a coronary artery extending through the myocardium and having pellets of therapeutic agent disposed around the artery.

FIGS. 5 and 6 depict more explicitly one method according to the invention for implanting a therapeutic agent into a tissue wall. The depicted method is a cardiovascular treatment for restenosis that can occur in a coronary artery. The method includes the steps of employing an elongate flexible surgical instrument (e.g., a catheter) having a distal end that carries a delivery chamber 14. The distal end is inserted into a vascular system of a patient, such as by insertion via a femoral artery or vein. The delivery chamber 14 is guided through the patient's vascular system until the delivery chamber 14 is disposed within the heart, such as within the left ventricle. Once within the heart, the delivery chamber is employed to implant a therapeutic agent into the tissue of the heart.

In a first step the physician can determine the therapeutic agent, or agents, to be implanted and the depot for the selected agents. The depot may be selected by considering, inter alia, the desired time of drug residence within the tissue and the desired dosage to be eluted during the course of the residence. Optionally, the pellets can carry a plurality of therapeutic agents, either by solidifying a plurality of agents within the polymer coating of each pellet, or by providing pellets carrying different therapeutic agents. This latter practice allows the physician to load both active therapeutic agents and agents capable of activating therapeutic agents upon contact, or capable of degrading the polymer wall of an implanted pellet. This can allow for greater time delay before activation of an agent, and for greater selection in the delivery vehicle and the agents and drugs being delivered. Once the agents are selected, the physician can select the delivery chamber to use and can pre-load the delivery chamber with a plurality of pellets, each of which can be a minisphere, a helical, conical pellet, a cylindrical container, or other device capable of being implanted into the myocardium. The physician can preload the delivery chamber 14 with the set of pellets that have been selected to deliver the proper depot of therapeutic agent to the tissue around an artery that is suffering from, or may suffer from, restentosis. Alternatively, pellets containing a desired therapeutic agent can be preloaded into the delivery system, which is provided to the physician as a sterile, disposable item.

Before delivering the preloaded delivery chamber 14 into the heart, the treating physician optionally performs a preliminary step of positioning a radio-opaque marker at the site of restenosis. This allows the treating physician to view the marker during delivery of the pellets. The marker can be a stent, or any viewable marker that will remain present at the site of the localized disease during the implanting of the drug delivery pellets.

In one practice, the marker can be the radio-opaque marker of a balloon being employed during a PTCA procedure. Specifically, as restenosis may arise from the site of the angioplasty, one practice of the invention performs the drug delivery at the same time as the angioplasty. In this procedure, the treating physician leaves the PTCA catheter in place, while the delivery implant system is guided to the target area. A radiopaque marker in the balloon gives fluoroscopic guidance during the implant procedure.

At this time, the physician can guide the implant system along the appropriate delivery route until the catheter enters the interior of the patient's heart. The delivery chamber can approach target areas from within any chamber of the heart. Notably, the practices described herein allow that even septal arteries can be treated for cardiac conditions or to stimulate angiogenisis. In FIG. 5, the delivery chamber is shown as approaching the target area from the interior of the heart, and positioning the delivery chamber against the endocardial tissue over the myocardium. Upon positioning the delivery chamber adjacent the interior tissue wall of the heart, the physician drives the delivery chamber into the tissue and to the targeted area. The physician actuates the control mechanism and ejects a pellet from the delivery chamber, implanting the pellet within the targeted area of the myocardium.

It is a realization of the present invention that the practices described herein are often suitable for arteries normally considered epicardial, with little surrounding myocardial tissue or subepicardial fat in which to implant the drug delivery pellets. Specifically, researchers have noted that tunneled epicardial coronary arteries may represent a normal variant being recognized in up to 86% of vessels. Waller, *Anatomy, Histology, and Pathology of the Major Epicardial Coronary Arteries Relevant to Echocardiographic Imaging Techniques*, Journal of American Society of Echocardiographic Imaging, vol. 2 (1989).

FIG. 6 illustrates a further realization of the present invention. FIG. 6 shows that it is desirable to implant the pellets as close as possible to the artery being treated, and that providing an array of implanted pellets about the periphery of the artery may provide sufficient localized elution of therapeutic agent to prevent restenosis. In one practice, the pellets are implanted through a single point of entry through the myocardium. The physician manipulates the distal tip of the catheter to dispose the port of the delivery chamber at the depicted locations. At each location, a pellet is ejected from the delivery chamber and implanted into the myocardium.

Figure 7:
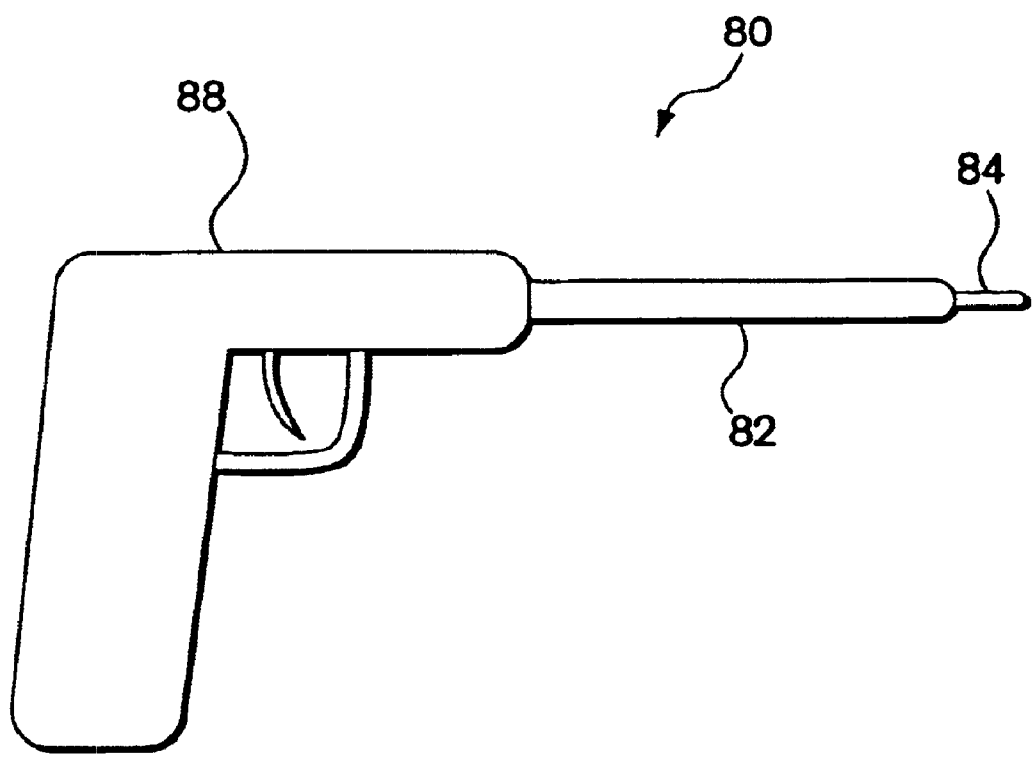
FIG. 7 depicts a local drug delivery device having a pistol grip and being suitable for use during an endoscopic procedure.

FIG. 7 depicts a further alternative embodiment of the invention. The depicted system 80 includes a short catheter 82 that carries a delivery chamber 84 at its distal end and that connects at its proximal end to a pistol grip control mechanism 88.

The system 80 is adapted for use during an endoscopic procedure and to that end the depicted catheter 84 is a short catheter adapted to slide within a endoscopic port that has been placed through the chest and positioned abutting the pericardium. The delivery chamber 84 can be a delivery chamber as discussed above and can be dimensionally adapted to penetrate and extend through the pericardial sac. The delivery chamber can penetrate into the myocardium and thereby allow the physician to implant pellets into the myocardium. Optionally, the catheter 82 can be a steerable catheter which allows the physician to bend the distal tip of the catheter 82 to place the delivery chamber 84 where needed. Alternatively, the catheter can include a deflectable tip, as is known in the art, which the physician can direct to the targeted area. Other modifications to the system 80, including providing the catheter with a fiber optic viewing device to allow the physician to view the interior of the pericardial sac, can be made without departing from the scope of the invention.

The depicted pistol grip 88 provides the physician with a manual actuator that allows the physician to control the implanting of pellets within the myocardium. The pistol grip 88 can be a molded plastic assembly of the type well known in the art for actuating a mechanical assembly, such as the plunger assembly of the delivery chamber 14 described above.

In a further practice, the techniques of the invention can be employed during an open chest procedure. Specifically, the surgeon performing the open chest operation can employ a delivery device that includes a delivery chamber as described above to implant pellets into the myocardium. Additionally, in this practice, the physician can employ a hypodermic needle to inject a solution containing microspheres of a therapeutic agent. Other practices of the invention can be practiced without departing from the scope thereof.

Moreover, the systems and methods for implanting depots of therapeutic agents can be applied to conditions other than those relating to cardiac failure. For example, the systems described herein can be applied to the treatment of muscle tissue afflicted by insufficient circulation. In one practice, the systems described herein are employed to deliver a human angiogenic growth factor, such as VGEF, which is understood to stimulate the growth of blood vessels. Thus, the systems described herein can promote the survival of muscle tissue that is moribund as a result of poor circulation due to failing or occluding blood vessels.

Those skilled in the art will know or be able to ascertain using no more than routine experimentation, many equivalents to the embodiments and practices described herein. For example, the devices described herein can be used in cooperation with drilling elements or laser devices capable of forming an opening in a tissue wall, such as the myocardium. The delivery chamber can be inserted into the preformed openings for delivering a therapeutic agent therein. Further, pellets according to the invention can include threaded exterior surfaces that facilitate implanting the pellet within a tissue wall. Accordingly, it will be understood that the invention is not to be limited to the embodiments disclosed herein, but is to be understood from the following claims, which are to be interpreted as broadly as allowed under the law.

I claim:

1. A therapeutic agent delivery apparatus and at least two therapeutic agents for delivery to tissue comprising:

a body formed of a biocompatible material containing at least two reservoirs each containing one of the therapeutic agents and being permeable to at least one therapeutic agent, wherein the first therapeutic agent contains the agent capable of promoting angiogenesis, and wherein the second therapeutic agent contains cells adapted for implantation in said tissue.

2. An apparatus according to claim 1 wherein said biocompatible material comprises a drug releasing compound capable of releasing at least one therapeutic agent.

3. An apparatus according to claim 2 wherein said drug releasing compound is capable of releasing at least one therapeutic agent capable of promoting angiogenesis.

4. An apparatus according to claim 1 wherein said biocompatible material is a bioresorbable material.

5. An apparatus according to claim 1 wherein said body includes at least a first and a second member, each having a respective one of said first and said second therapeutic agents.

6. An apparatus according to claim 1 wherein at least one reservoir contains molecular ligands, said ligands possessing specific affinity for cell surface markers expressed on circulating myocyte precursor cells, whereby said myocyte precursor cells become affixed within said reservoir.

7. A therapeutic agent delivery apparatus and at least one therapeutic agent for delivery to tissue comprising:

a pellet formed from a biocompatible material with a plurality of surfaces for contacting the tissues to promote localized angiogenesis, a reservoir disposed within said pellet adapted for delivering cells capable of implantation in the tissue, and skeletal myoblast-derived cells capable of implantation in the tissue carried by the reservoir.

8. A therapeutic agent delivery apparatus and at least one therapeutic agent for delivery to tissue comprising:

a pellet formed from a biocompatible material with a plurality of surfaces for contacting the tissues to promote localized angiogenesis, a reservoir disposed within said pellet adapted for delivering cells capable of implantation in the tissue, and cardiomyocyte cells capable of implantation in the tissue carried by the reservoir.

9. A therapeutic agent delivery apparatus and at least one therapeutic agent for delivery to tissue comprising:

a pellet formed from a biocompatible material with a plurality of surfaces for contacting the tissues to promote localized angiogenesis, a reservoir disposed within said pellet adapted for delivering cells capable of implantation in the tissue, and precursors to cardiomyocyte cells capable of implantation in the tissue carried by the reservoir.

10. A therapeutic agent delivery apparatus and at least one therapeutic agent for delivery to tissue comprising:

a pellet formed from a biocompatible material with a plurality of surfaces for contacting the tissues to promote localized angiogenesis, a reservoir disposed within said pellet adapted for delivering cells capable of implantation in the tissue, and genetically modified fibroblast cells capable of implantation in the tissue carried by the reservoir.

11. A therapeutic agent delivery apparatus and at least one therapeutic agent for delivery to tissue comprising:

a pellet formed from a biocompatible material with a plurality of surfaces for contacting the tissues to promote localized angiogenesis, a reservoir disposed within said pellet adapted for delivering cells capable of implantation in the tissue, and precursors to fibroblast cells capable of implantation in the tissue carried by the reservoir.

12. A therapeutic agent delivery apparatus and at least one therapeutic agent for delivery to tissue comprising:

a pellet formed from a biocompatible material with a plurality of surfaces for contacting the tissues to promote localized angiogenesis, a reservoir disposed within said pellet adapted for delivering cells capable of implantation in the tissue, and bone marrow stromal cells capable of implantation in the tissue carried by the reservoir.

13. An apparatus according to claim 7 wherein said biocompatible material comprises a drug releasing compound capable of releasing at least one therapeutic agent.

14. An apparatus according to claim 13 wherein said drug releasing compound is capable of releasing at least one therapeutic agent capable of promoting angiogenesis.

15. An apparatus according to claim 7 wherein said biocompatible material is a bioresorbable material.

* * * * *

UNITED STATES PATENT AND TRADEMARK OFFICE
CERTIFICATE OF CORRECTION

PATENT NO. : 6,689,121 B1
DATED : February 10, 2004
INVENTOR(S) : Cafferata

It is certified that error appears in the above-identified patent and that said Letters Patent is hereby corrected as shown below:

Title page,
Item [56], References Cited, U.S. PATENT DOCUMENTS, add the following patent numbers:

| | | |
|---|---|---|
| -- 5,980,548 A | 10/1997 | Evans |
| 6,248,112 B1 | 06/2001 | Gambale et al. |
| 6,277,082 B1 | 08/2001 | Gambale |
| 6,432,126 B1 | 08/2002 | Gambale et al. |
| 6,447,522 B1 | 09/2002 | Gambale et al. |
| 6,458,092 B1 | 10/2002 | Gambale et al. -- |

Signed and Sealed this

Twenty-sixth Day of October, 2004

JON W. DUDAS
*Director of the United States Patent and Trademark Office*